United States Patent
Shaw

(10) Patent No.: US 8,561,230 B2
(45) Date of Patent: *Oct. 22, 2013

(54) MATTRESS MONITORING SYSTEM

(76) Inventor: Mark Shaw, Poland, OH (US)

(*) Notice: Subject to any disclaimer, the term of this patent is extended or adjusted under 35 U.S.C. 154(b) by 53 days.

This patent is subject to a terminal disclaimer.

(21) Appl. No.: 13/217,382

(22) Filed: Aug. 25, 2011

(65) Prior Publication Data

US 2012/0078421 A1 Mar. 29, 2012

Related U.S. Application Data

(63) Continuation of application No. 12/021,724, filed on Jan. 29, 2008, now abandoned, which is a continuation-in-part of application No. 10/982,085, filed on Nov. 5, 2004, now Pat. No. 7,346,944.

(51) Int. Cl.
*A61G 7/00* (2006.01)

(52) U.S. Cl.
USPC .......................................... 5/616; 340/825.52

(58) Field of Classification Search
USPC .......................................... 5/616; 340/825.52
See application file for complete search history.

(56) References Cited

U.S. PATENT DOCUMENTS

| | | |
|---|---|---|
| 5,787,528 A | 8/1998 | Antinori |
| 5,848,450 A | 12/1998 | Oexman et al. |
| 6,378,152 B1 | 4/2002 | Washburn et al. |
| 6,393,224 B1 | 5/2002 | Stern et al. |
| 6,396,224 B1 * | 5/2002 | Luff et al. ................... 318/16 |
| 6,876,303 B2 | 4/2005 | Reeder et al. |
| 7,010,369 B2 | 3/2006 | Borders et al. |
| 7,017,208 B2 | 3/2006 | Weismiller et al. |
| 7,346,944 B2 | 3/2008 | Shaw |
| 2002/0014951 A1 | 2/2002 | Kramer et al. |
| 2003/0076238 A1 | 4/2003 | Moster et al. |
| 2003/0195644 A1 | 10/2003 | Borders et al. |

* cited by examiner

*Primary Examiner* — Michael Trettel
(74) *Attorney, Agent, or Firm* — Shannon V. McCue; Hahn Loeser & Parks LLP

(57) ABSTRACT

A system for monitoring a mattress controller including a portable monitor having a memory, an input/output node in selective communication with the mattress controller, a processor programmed to maintain in the memory a data structure including a control data associated with the mattress controller, and selectively link with the mattress controller to communicate with the mattress controller to confirm or update the control data.

20 Claims, 12 Drawing Sheets

MATTRESS MONITORING SYSTEM

RELATED PATENT APPLICATIONS

This application is a Continuation of U.S. patent application Ser. No. 12/021,724, filed on Jan. 29, 2008, which is a Continuation-in-part of U.S. patent application Ser. No. 10/982,085, filed Nov. 5, 2004, now U.S. Pat. No. 7,346,944, incorporated by reference, as if fully rewritten herein.

TECHNICAL FIELD

In general, the present invention relates to a system for monitoring the function of a therapeutic mattress and controller. More particularly, the present invention relates to a mattress monitoring system that monitors the operation of a mattress including controller functions. Most particularly, the present invention relates to a mattress monitoring system that uses a hand held wireless monitor that communicates with a mattress controller to obtain, report, and modify operating settings and other information relating to the mattress and controller.

BACKGROUND OF THE INVENTION

Therapeutic air mattresses have been used in connection with hospital beds or incorporated therein to provide patient support, reduce the likelihood of decubitus sores, and perform other therapeutic functions. These mattresses are connected to a blower or blower that pressurizes one or more inflatable portions of the mattress for a given therapeutic function. For example, the mattress depicted in U.S. Pat. No. 5,154,900 includes a pair of longitudinally extending bladders that are used to laterally turn a patient in an alternating fashion to reduce the likelihood of decubitus sores. In this application, the blower selectively pressurizes one or both of the bladders to an extent necessary to provide the desired degree of rotation or support. As will be appreciated, the pressure needed to support the patient will vary depending on a given patient's size and weight. Currently, to accommodate different weight capacities separate blowers designed to produce the necessary pressures are provided. It would be desirable to have a system that could be easily reprogrammed to support different weight capacities without having to stock multiple blowers.

In existing mattress systems, the pressure settings may include pressure increment levels that are preprogrammed on to a chip within the mattress controller. For example, an increment of 15 mm/Hg may separate high, medium, and low settings. The base pressure level may also be hard-coded on to the chip. Using the previous example, the lowest setting might be 10 mm/Hg, and the medium and high settings each being 15 mm/Hg increments from the previous setting. To change the settings that are programmed on to the chip, it is generally necessary to remove the chip and have it reprogrammed. This process requires a significant level of technical proficiency. Also, due to their sensitive nature, the chips must be carefully handled, and are prone to damage. If a setting must be changed, the caregivers generally rely on outside service people or the manufacture to reprogram the settings. During that time, the product may be out of use resulting in a cost to the caregiver. To that end, a simpler method of reprogramming pressure values for a given patient would provide greater flexibility to caregivers.

It is desirable to track the function of the mattress, blower, and controller. For example, since therapeutic beds are often operated on a rental basis, it is desirable to know the actual operating time for a given mattress. This time is also useful in determining whether a mattress or blower needs to be repaired or replaced. While such information could be tracked manually, it is highly desirable to have an automated method of monitoring the mattress system.

SUMMARY OF THE INVENTION

In light of the foregoing, it is an object of the present invention to provide a mattress monitoring system that provides a simple mechanism for changing pressure settings for a given patient.

It is another object of the present invention to provide a mattress monitoring system that tracks operational data received from the mattress.

BRIEF DESCRIPTION OF THE DRAWINGS

For a complete understanding of the objects, techniques and structure of the invention, reference should be made to the following detailed description and accompanying drawings wherein.

DETAILED DESCRIPTION OF THE INVENTION

Figure 1:
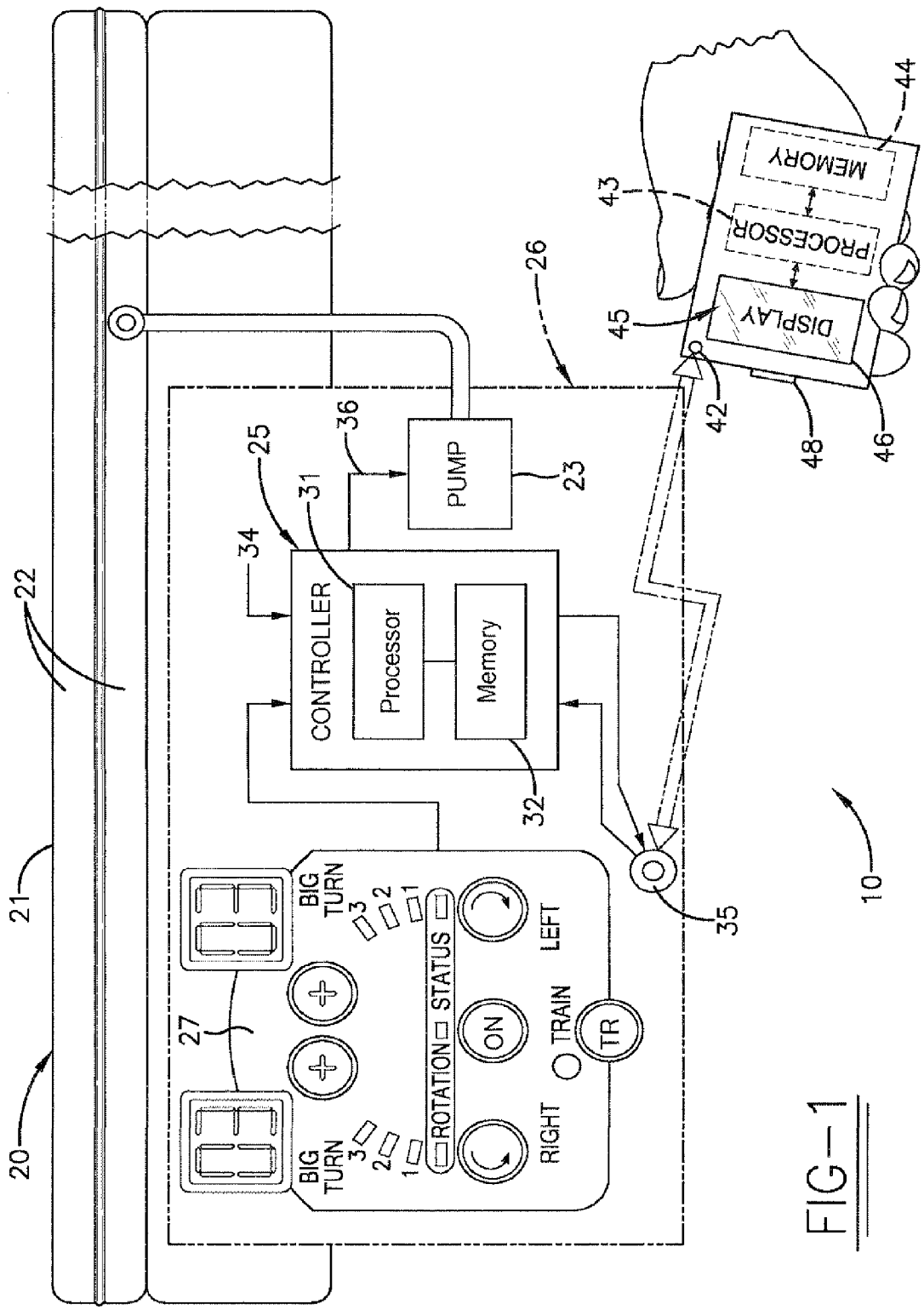
FIG. 1 is a schematic overview of a mattress monitoring system including a mattress controller and monitor according to the concepts of the present invention used in connection with a therapeutic mattress system.

The monitoring system of the present invention may be used in connection with patient support systems including without limitation hospital beds, mattresses, mattress overlays, therapeutic mattresses and pads, and bed frames. For purposes of example, the system is described in the context of a therapeutic mattress system. To that end, references will be made to use of the system of the present invention in connection with a bed or mattress. These references should be understood as encompassing patient support systems in general as well as the particular examples described.

A mattress monitoring system according to the concepts of the present invention is generally indicated by the numeral 10 in the accompanying drawings. With reference to the example shown in FIG. 1, the mattress monitoring system 10 is used in connection with a therapeutic air mattress system, generally indicated by the numeral 20. Mattress system 20 may be any of a variety of air mattress systems available in the art including the system disclosed in U.S. Pat. No. 5,154,900, which is incorporated herein by reference. The mattress system depicted in FIG. 1 will be described in general terms. Mattress system 20 includes a mattress 21 having one or more inflatable chambers 22. These chambers 22 are connected to an air source, such as a blower 23. The blower 23 is controlled by a controller, generally indicated by the numeral 25.

Controller 25 includes a housing, 26 which may also enclose the blower 23. Controller 25 may include a manually operable control input 27 such as buttons, touch pads, switches, or dials used to control various functions of the blower and/or mattress. For example, the controller 25 may include a control input 27 that provides a range of pre-set pressure levels to be maintained in the chambers 22. The control input may be connected to controller 25 of the mattress system 20. This controller 25 may include a processor 31 having additional inputs 34 and outputs 36, other than those discussed above, corresponding to bed operation. For example, input 34 may be a pressure sensor that monitors the pressure level within a chamber 22 and conveys that information to processor 31. The processor 31 may then send a signal via output 36 to the blower 23 to vary the delivery of air to the chamber 22 and adjust the pressure in the chamber 22. For example, the speed of the blower 23 may be varied to achieve the desired pressure.

Figure 3:
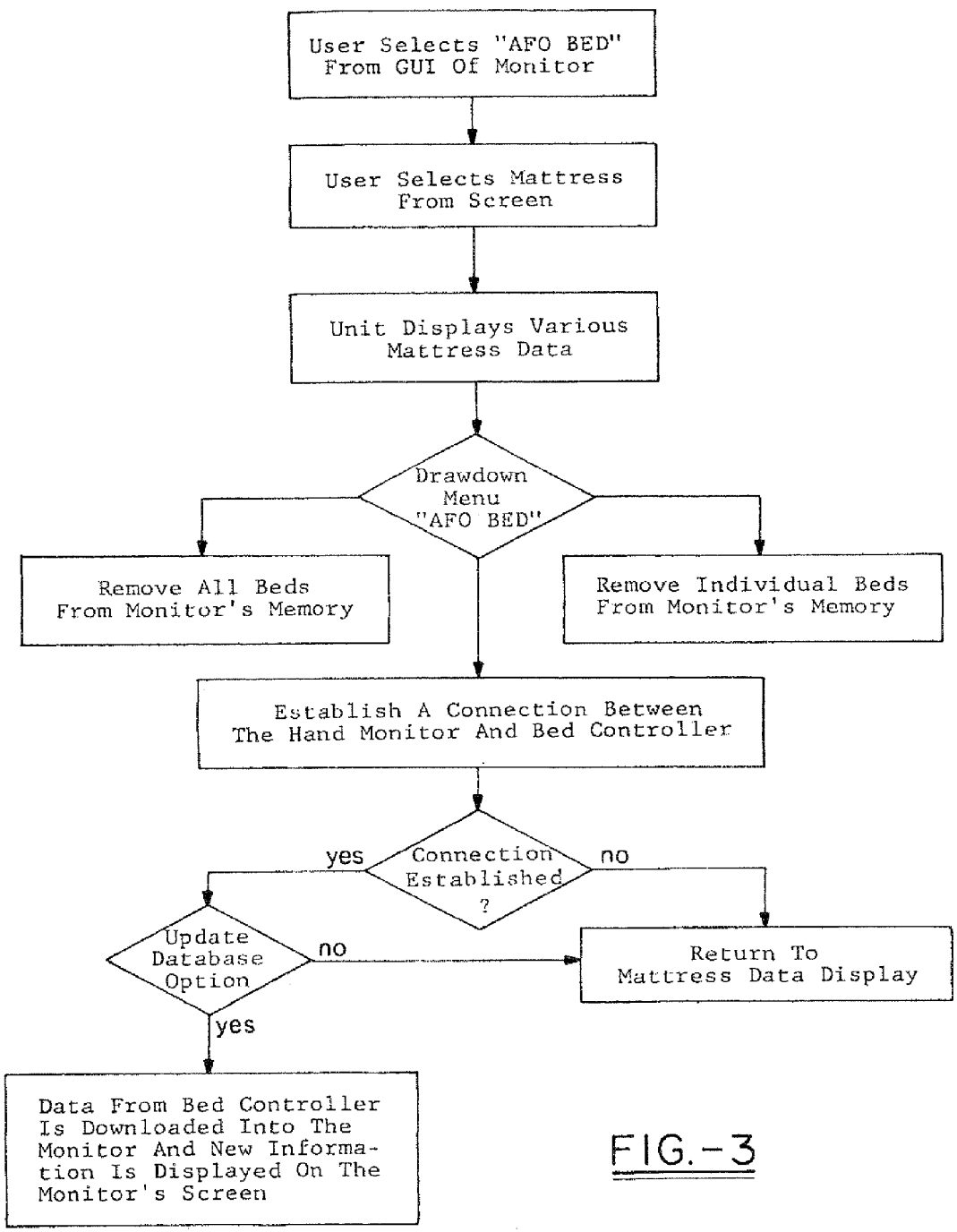
FIGS. 3, 4A, and 4B are flowcharts depicting the operation of aspects of a monitoring system according to the concepts of the present invention.

The controller 25 may further include a memory 32 that communicates with the processor 31. The memory 32 may be any computer readable medium, including but not limited to RAM, ROM, Flash Rom, EEP Rom, a storage diskette, compact disk, hard drive, chip drive, tape, MEMORY STICK® or any other type of volatile or non-volatile memory. The memory 32 may store data representing a bed identification BI, modes of operation, pressure values, time and date information, bed or mattress position, blower operation information, such as time of activation or deactivation, operating time, alarm conditions, button pushes, and blower speed(s), and other information or functions of interest to the user. For sake of simplicity, these and further data generated by processing these data are collectively are referred to as "control data" and generally indicated by the letters CD. When discussing control data CD for a specific bed identification BI, the control data CD may be referred to as a setting, for example FIG. 3, such references are used in connection with the depicted example and should not be considered limiting.

The memory 32 may store one or more control data CD in a separate field accessible by the processor 31. For example, a first field might include the bed identification BI, such as a name, number, or other readable indicia representing a particular bed; a second field might include a mode of operation, pressure setting, time stamp, date stamp, or blower information. If necessary, another field may be used to correlate plural fields. For example, a third field may correlate first and second fields, such that the bed identification BI is associated through third field with the other control data CD found in the second field. Still another field may store data produced by comparing control data stored in the monitor's memory 44 with control data CD stored in the controller's memory 32.

The controller 25 may further monitor the use of the control input 27. For example, in a system that uses buttons for the control input 27 (FIG. 1), the controller 25 may monitor the number of times each button is pushed and the time that this event occurred. This control data CD could then be stored in the memory 32, as an additional field.

The controller 25 may also include embedded software that creates a data structure, which would be stored in memory 32, for selected control data CD that are of interest to the user. For example, the data structure may record hours of operation, operational settings, such as pressure, turn interval, degree of turn, date and time stamps for each operation, and any alarm conditions occurring during operation. The data structure created by the software may then be stored in memory 32 for later retrieval, as described more completely below. The embedded software could be implemented using a variety of high or low-level programming languages, including but not limited to assembly, C, C++, Fortran or the like.

The controller 25 is adapted to communicate with a portable monitor, generally indicated by the numeral 40. To that end, both the controller 25 and monitor 40 respectively include an input/output node 35, 42, which may be a wireless transceiver, as shown in FIG. 1. The wireless transceivers may suitably use any known wireless communication protocol, such as light, radio, or sonic waves, infrared; RF; or other signal technologies. The controller 25 may be made compliant with various industry standards so that it can work with a variety of devices. For example, for infrared devices, an IrDA compliant system may be implemented in controller 25 to work with various infrared devices.

Figure 7:
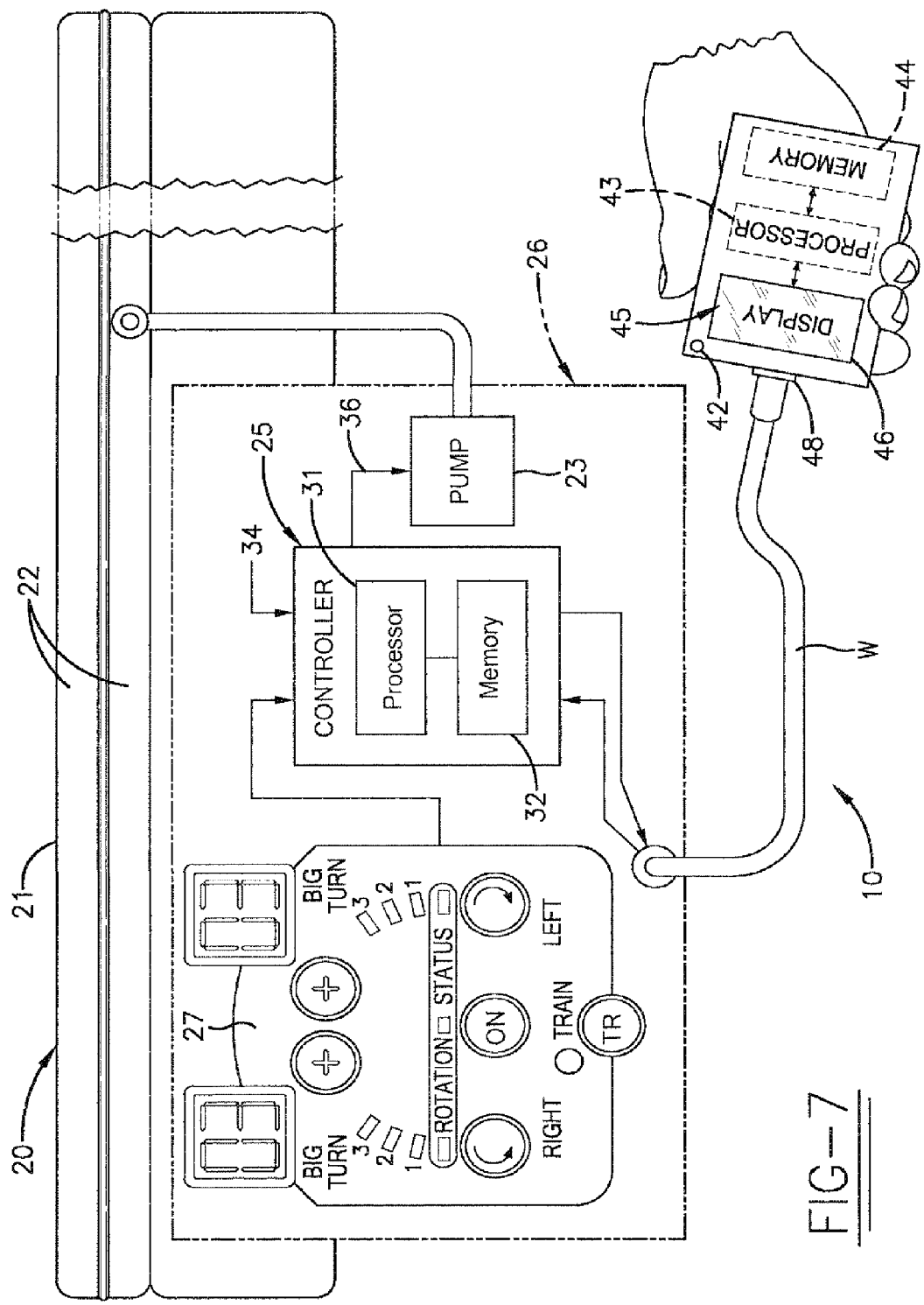
FIG. 7 is a schematic overview similar to FIG. 1 depicting an alternative embodiment of a mattress monitoring system including a mattress controller and a portable monitor according to the concepts of the present invention.

Alternatively, controller 25 and monitor 40 may communicate via a serial cable, USB cable, modular cable, fiber optic cable, or other physical connection between the input/output nodes 35, 42. For example, as shown in FIG. 7, a non-wireless connector W may be used. Connector W may include one or more plugs or adapters that allow the monitor 40 to be selectively connected to controller 25. To that end, the input/output nodes 35, 42 may include a suitable outlet or port that receives the plug or adapter.

A suitable monitor 40 would include a processor 43 connected to memory 44 and the transceiver 35, 42. Monitor 40 may further include a system for conveying information to the user including audio, visual, mechanical, or other means, collectively referred to as a "display" 45, herein. In the embodiment depicted in the Figures, a visually perceived display screen 46 is used. In this example, the monitor 40 is a hand-held computer, which incorporates all of the above described components in a single hand-held device, such as a personal digital assistant, but other devices having the suitable processing, memory, and communication abilities could be used or a custom device constructed for use as a monitor 40. It will be appreciated that the above described components do not have to be incorporated into a single unit.

Figure 5A:
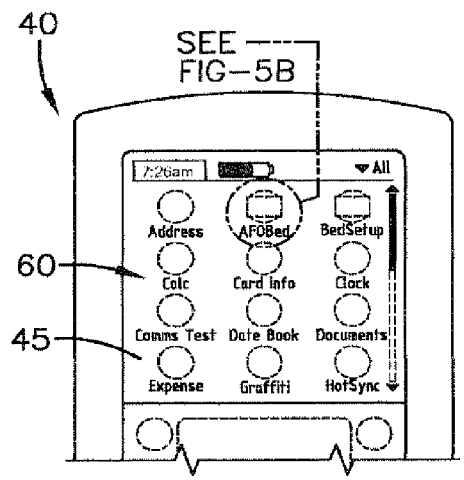
FIGS. 5 and 6 are schematic overviews depicting a monitor having a graphical user interface according to the concepts of the present invention.
Figure 5B:
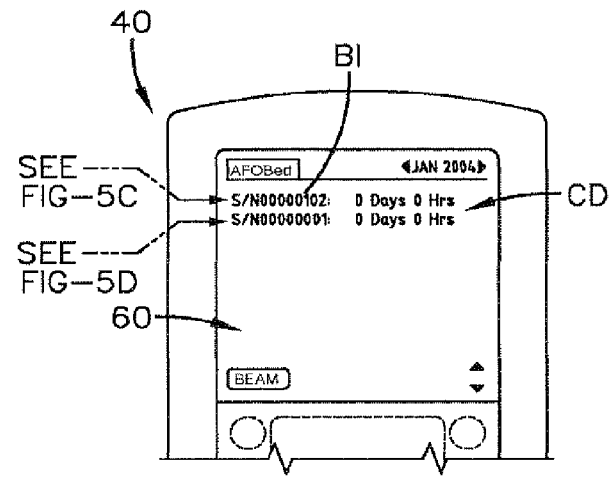
Figure 5C:
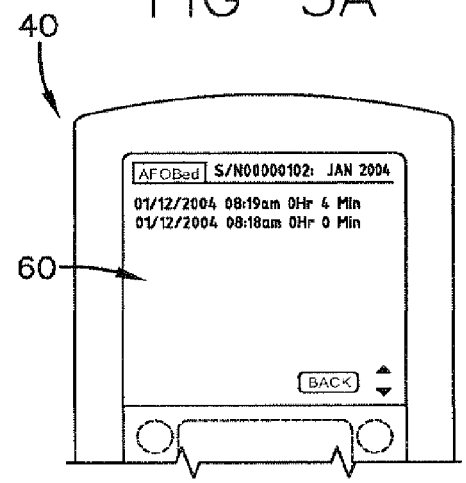
Figure 5D:
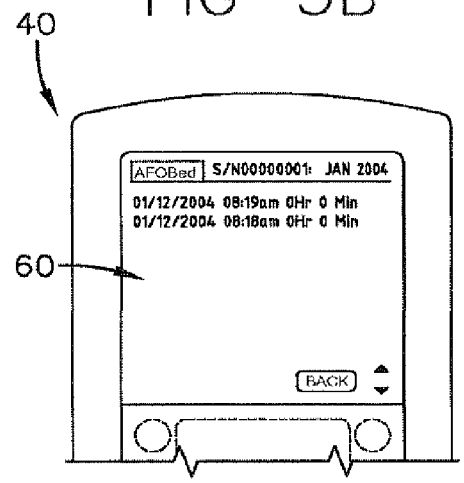
Figure 5E:
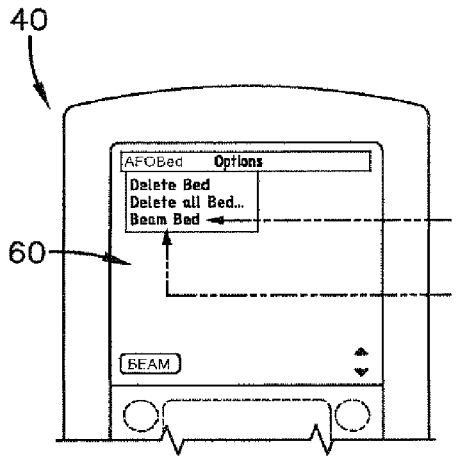
Figure 5F:
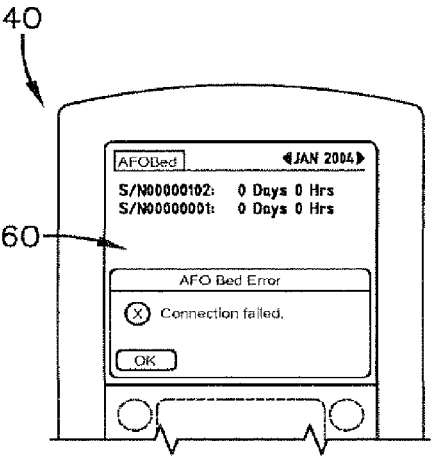
Figure 5G:
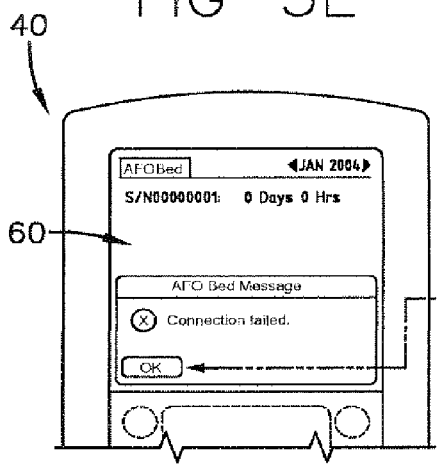
Figure 5H:
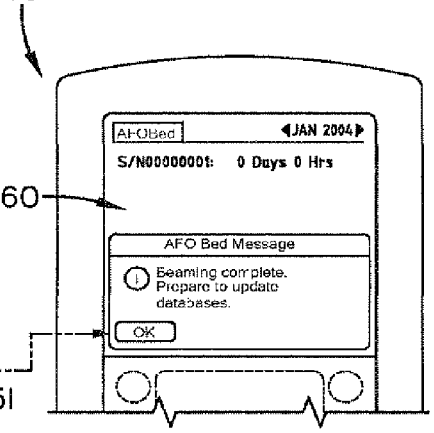
Figure 5I:
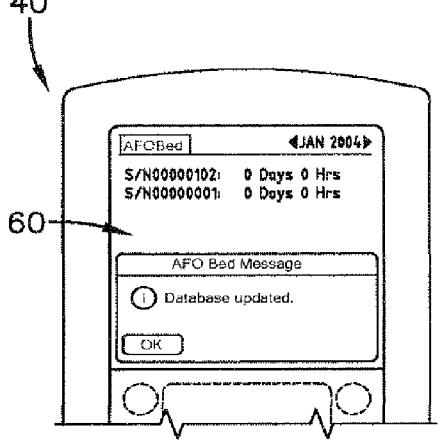
Figure 5J:
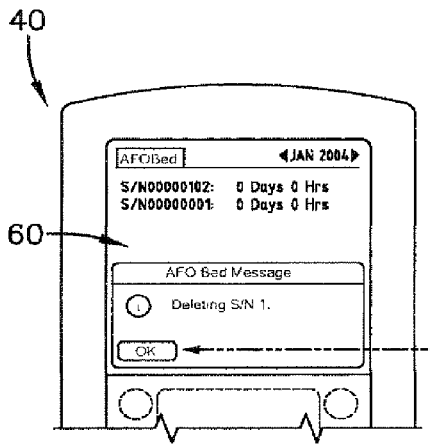
Figure 5K:
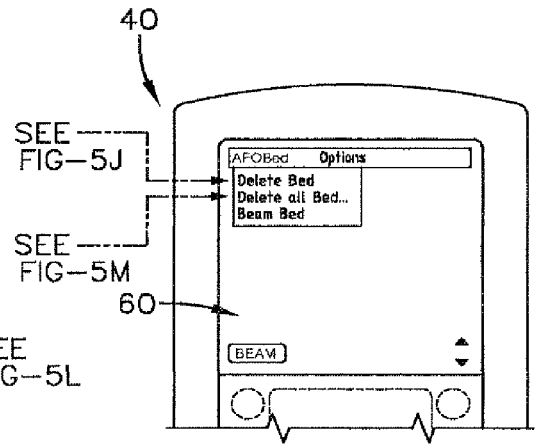
Figure 5L:
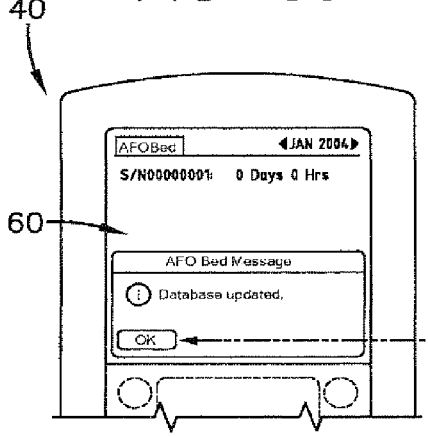
Figure 5M:
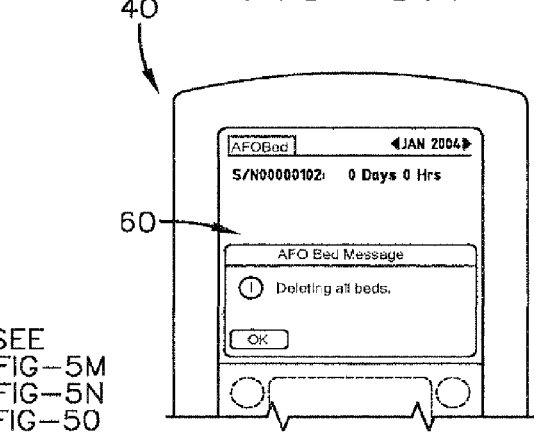
Figure 5N:
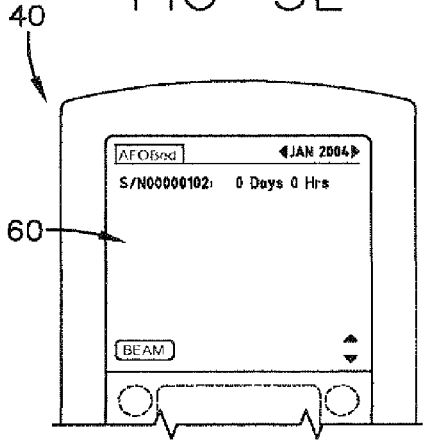
Figure 5O:
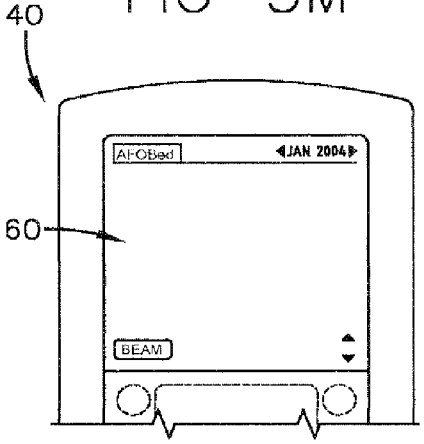
Figure 6A:
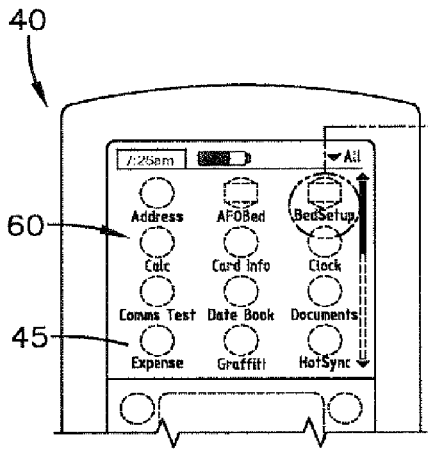
Figure 6B:
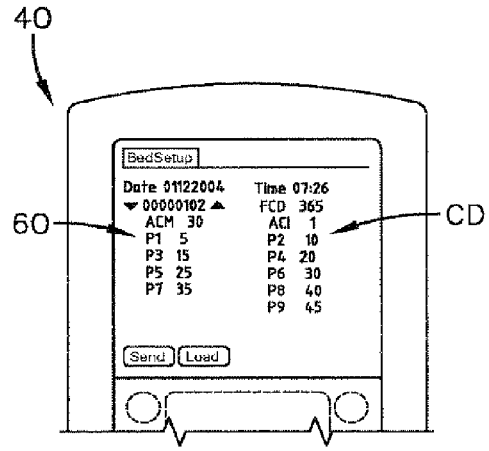
Figure 6C:
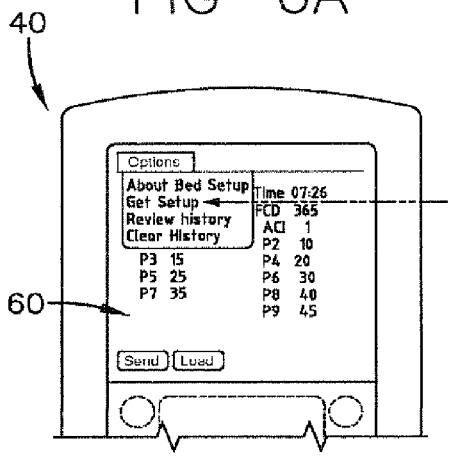

The monitor 40 is adapted to selectively transmit or receive control data CD to or from the controller 25. For example, the control data CD might include a bed identifier BI, such as a serial number (FIG. 5B, 6B), set time, set cycle time range, set cycle time intervals, pressure settings, and other settings, as desired by the user. This control data CD may be stored in the monitor's memory 44. As described with respect to control memory 32, memory 44 may store the control data CD as a data structure having one or more fields, ($F_1 \ldots F_n$). These fields ($F_1 \ldots F_n$) may correlate to those in control memory 32, such that, for example, the first field ($F_1$) in both memories 32, 44 includes the bed identification BI. The monitor 40 may be adapted to track user history logs and download the embedded data logs from the control unit 25.

The above steps may be programmed into the memory 44 of the monitor 40 or contained on removable memory, such as, a portable storage disk, MEMORY STICK®, portable hard drive, Flash Rom, EEP Rom, or other portable storage media that may be used with one or more monitors 40. The monitor 40 may be adapted to synchronize with a computer 50 to provide greater functionality to the user. For example, the monitor 40 may be adapted to transmit the settings and data log to the computer 50. The computer 50, in turn, may be adapted to take the settings and data logs and generate various reports of control data CD, as desired by the user.

For example, the computer 50 may display usage for an air mattress organized by serial number. These reports may track and update the usage of a given air mattress and control unit 25 over its entire life span or for a period of time selected by the user.

The computer 50 may send information to the monitor 40 using the wireless communication methods described above or a serial, USB or other physical connection. Again, this information may be keyed to the air mattress serial number, such that specific settings for individual air mattresses may conveniently be updated at a single computer 50 and then the portable monitor 40 is used to transfer this information to the individual air mattress controller 25.

One example of the method of operation stored in monitor's memory will now be described with reference to FIGS. 3-6. the terminology used in connection with the monitor 40 and displayed to the user are used as an example, and are not limiting as other terms may be used interchangeably by those of ordinary skill.

To facilitate use of the monitor 40, the monitor 40 may be provided with a graphical user interface 60 (FIGS. 5-6) that may display the information from one or more mattresses 21. An example of the operable steps of monitor 40 are outlined in FIGS. 3-4 and will be described in conjunction with FIGS. 5-6, which show an example of a suitable graphical user interface 60. These steps and interface 60 are shown for purposes of example and are not to be considered limiting. In the example shown, the monitor 40 may provide separate viewing and setup operations, accessible for example, by the "AFO Bed" and "Bed Setup" icons on the graphical user interface 60. It will be appreciated that a single program could include both operations or combine aspects of these operations. In the example shown, upon selection of AFO Bed, the graphical user interface 60 may display a list of bed identification BI allowing the user to retrieve information according to the bed identification BI. Upon selecting a bed or mattress, the graphical user interface 60 may display selected control data CD for one or more mattresses 21. For example, as shown in FIG. 5, the graphical user interface 60 may include a first screen 61 displaying one or more mattresses 21 separately identified, for example, by serial number. The user may select a desired mattress in a variety of commonly used methods including alphabetical or numerical entry corresponding to a given mattress 21, scrolling through the list and selecting the mattress, for example, with a jog shuttle or mouse selection device, touching a selected air mattress 21 displayed on a touch screen, or entering a mattress name or serial number via a keyboard or pad. A number of selection devices including the mouse, touch screen, keyboard, pad, and jog shuttle devices described above are available and will be collectively referred to as a "selection device."

Figure 2:
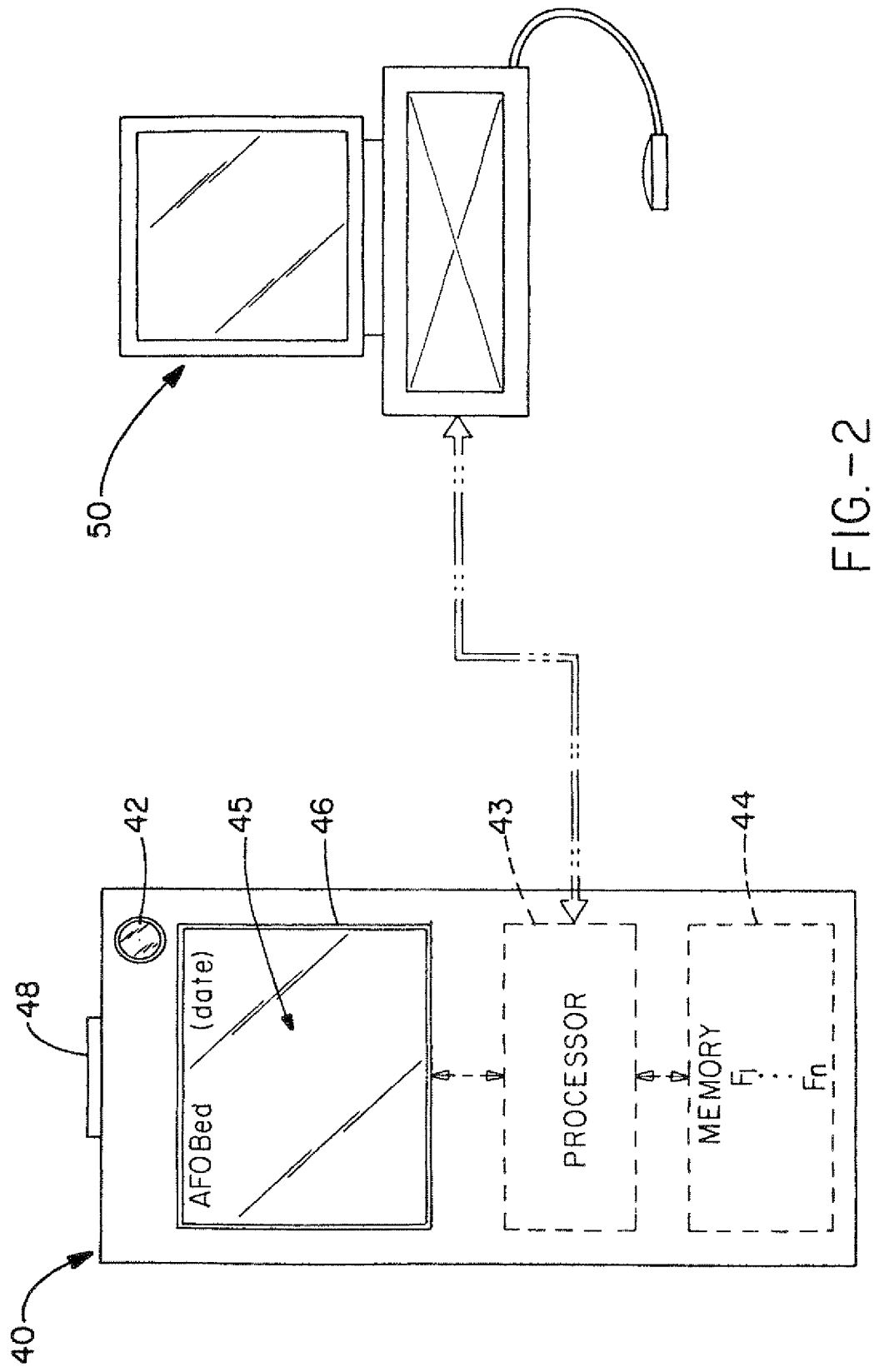
FIG. 2 is a schematic overview of a monitor according to the concepts of the present invention shown in communication with a computer.

It will be appreciated that the monitor 40 may be adapted to include one or more of these methods for selecting a given air mattress 21. After selecting a given air mattress 21, the graphical user interface 60 displays selected information about the air mattress 21. For example, as shown, information stored within the monitor's memory 44 for a given mattress 21 may be displayed on a separate screen or window (FIG. 1) including the date stamp for the bed's start-up and operation. The user may then select a mattress using any one of the methods described above to connect with the mattress 21 via the wireless transceiver 42. In the example shown in FIG. 2, this command is located within a pull down menu and referred to as "beam bed." As shown, if the monitor 40 fails to connect, an error message may be displayed on the graphical user interface 60. Likewise, a successful connection causes the graphical user interface 60 to display a "connection established" message and prompts the user to proceed to the next menu. If the user authorizes the monitor 40 to proceed, the mattress information and settings are transferred to the monitor 40 and the user is prompted to authorize updating of the monitor's memory 44.

If the user authorizes the update, the databases or data structures within memory 44 are updated and the new information is displayed on the graphical user interface 60.

If a mattress is no longer in use or the user wishes to clear this mattress from memory 44, the graphical user interface 60 may provide the user with the option of deleting the mattress 21 from memory 44 by selecting the "delete bed" command on the menu of the graphical user interface 60. Also, the graphical user interface 60 provides a "delete all beds" command to completely clear the monitor's memory 44.

Additional screens may be provided to display the control data CD and allow the user to alter this control data CD on the graphical user interface 60 and authorize updating of the control data CD within the controller's memory 32 by transferring the altered control data CD to the controller 25. In this way, the control data CD including operational settings, such as pressure values, blower speeds etc. within controller 25 may be reset without the difficulty of removing a control chip and reprogramming it.

Figure 4A:
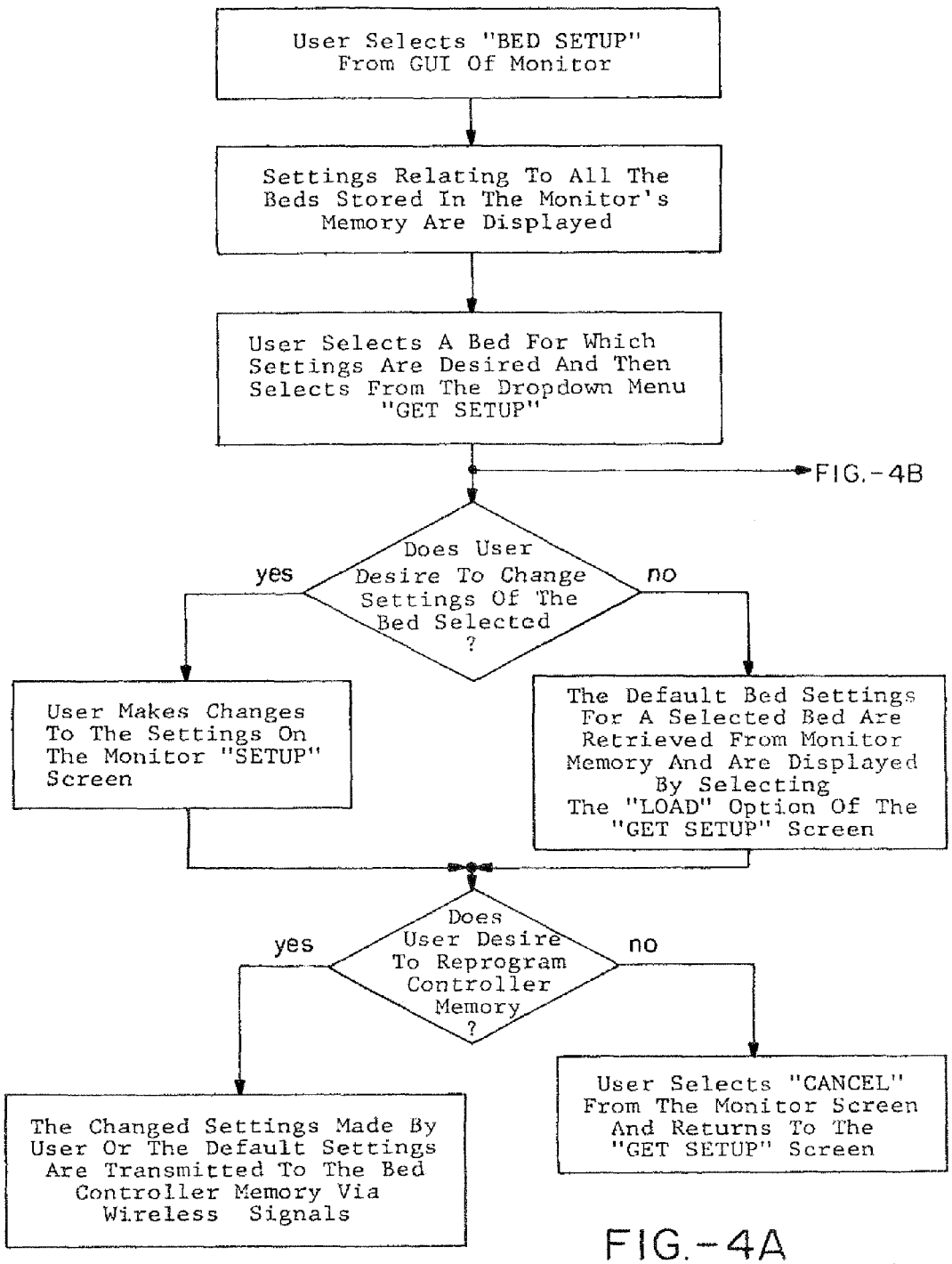
Figure 4B:
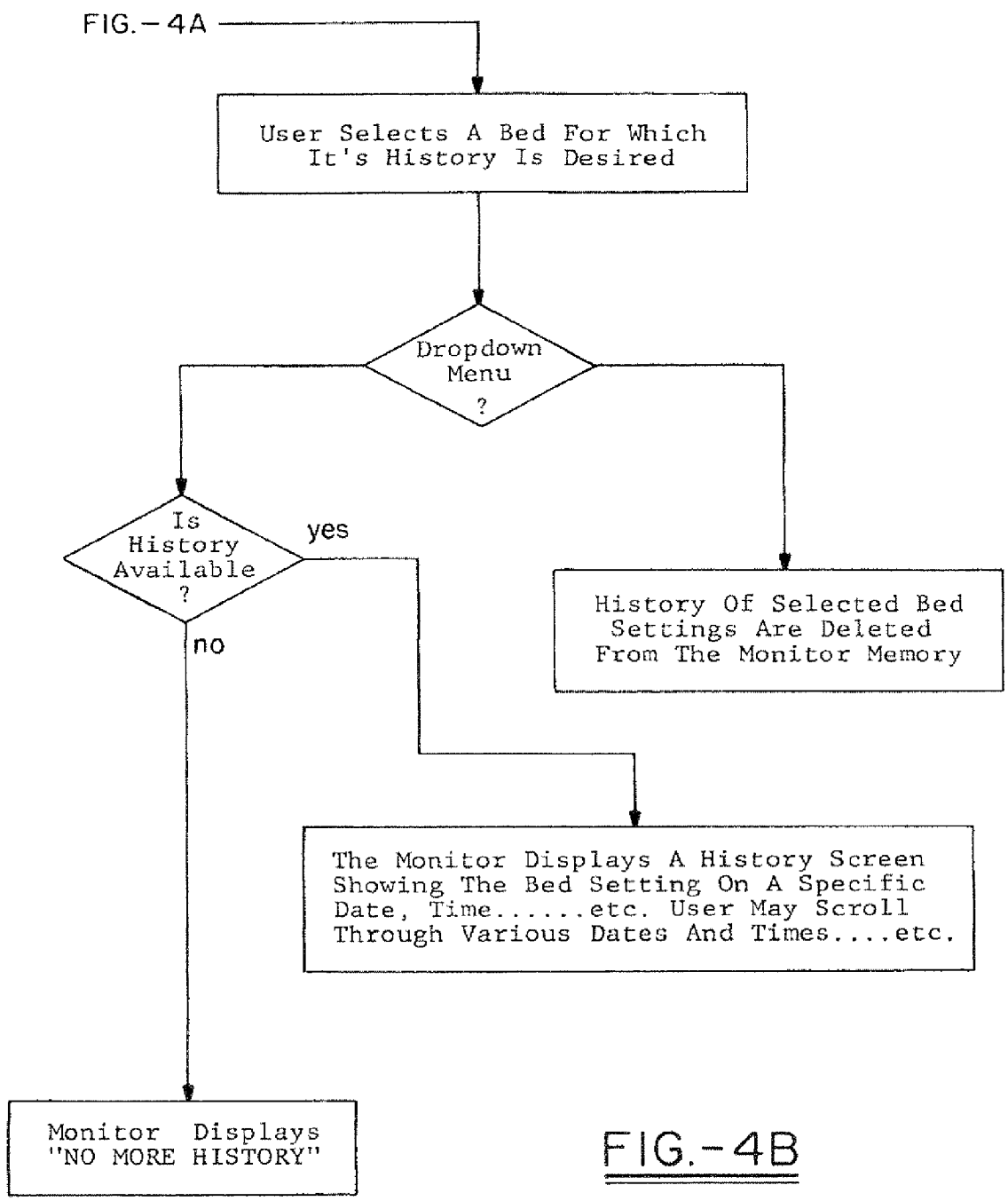

A method of setting up a bed is outlined in FIGS. 4A and 4B and a corresponding graphical user interface is depicted in FIG. 6. To facilitate practice of this method, a graphical user interface 60 may be provided with screens, as depicted in FIGS. 6A-6J to guide the user through the setup process. For example, as shown in FIG. 6A, a bed setup icon may be displayed on the graphical user interface 60 and selected, in a known manner, such as touching the screen, to enter the bed setup process. Upon entering the bed setup process, as depicted in FIG. 6B, the graphical user interface displays control data CD relating to a bed(s) stored in memory. This information may include default settings for any bed or current settings for a particular bed including the date, time and identification of the bed, such as, a serial number. Additional information may include maintenance information for the bed, including the number of days until the filter needs to be changed or filter change days (FCD), the maximum alternate cycle (ACM), alternate cycle increment (ACI) and pressure settings, for example, P1-P9, which may correspond to a pressure range indicator(s) provided on the controller 25, for example a series of LEDs (FIG. 1). In this way, the pressures corresponding to each point in the range may be viewed via the graphic user interface 60, and adjusted, as described more completely below.

The monitor 40 may be used to retrieve and alter control data CD for a selected bed. This control data CD may be retrieved from memory 44 or memory 32. When retrieving control data CD from memory 32, monitor 40 prompts the controller 25 via transceivers 35, 42. In the example shown, the graphical user interface 60 includes a pull down menu with the command "get setup" which may be selected by touching the screen 46. In the graphical user interface 60, shown, the control data CD is displayed with send and load commands indicated on the screen. By selecting the load command, the user will load the monitor 40 with default bed settings for the particular bed from the monitor's memory 44. To cause the user to view all other information before sending or loading control data CD, these commands may be located near the bottom of the graphical user interface 60. After loading the control data CD, the user may be given the choice of keeping the control data CD or returning to the previous settings. In the example shown, a "done getting setups" window (FIG. 6D) is displayed with the choice of selecting "okay" to accept the loaded control data CD or "cancel" to return to the previous control data CD. After selecting "okay", the default control data CD is displayed on the graphical user interface 60.

Figure 6D:
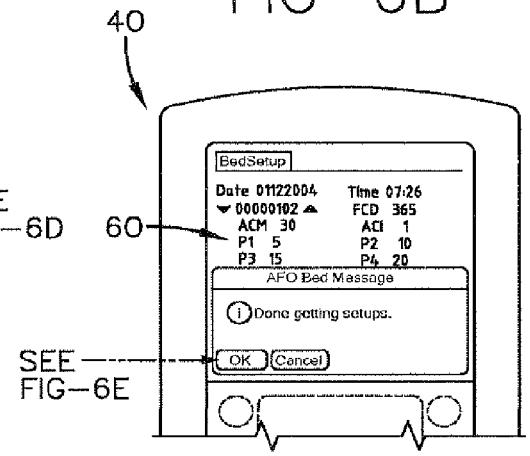
Figure 6E:
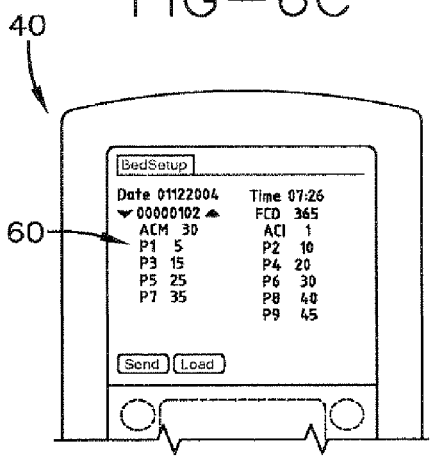

To alter the control data CD, the user may enter new values on the setup screen and then select "send" (FIG. 6K) to overwrite the current values stored in bed controller memory 32. For example, a patient may require different pressures, bed angles, alternating speeds, or cycle times. To change these values the user may input new values for the control data CD and then transfer the altered control data CD to the controllers 25 to change the control data CD in memory 32. To prevent accidental overwriting, a window may be used to verify entry of the new settings. For example, as shown in FIG. 6L, a bed message may be displayed indicating that sending the settings will overwrite current values and require the user to confirm their desire to change the control data CD by clicking on "okay." If the user does not wish to send the control data CD, a "cancel" button may be provided to return to the original settings. Once the user has completed sending the control data CD, they may be prompted to confirm that they have finished getting control data CD, for example, the monitor 40 may display "done getting setups" as shown in FIG. 6D. If the user indicates that they are done, the monitor 40 may exit the get setup program. If the user indicates that they are not done, the monitor 40 may return to the last displayed window or a main menu to allow the user to continuing getting setups.

According to the concepts of the present invention, a method of reviewing the history of each bed may also be provided. This method may be stored in any computer readable medium and may include the programmable steps outlined as an example in FIG. 4B. In the example monitor 40, shown in FIGS. 6F-6J, the history may be accessed via the same graphical user interface as the bed setup. For example, the pull down menu may include a "review history" command that allows the user to access bed history. As shown, upon selecting the "review history" command, the graphical user interface 60 displays a history screen showing the bed control data CD on a particular date and time. The user then may page through or scroll through control data CD associated with other days. In the example shown in FIG. 6H, arrow keys are provided at the top right corner of the graphical user interface 60 within the history bar that displays the date and time. In this way, the user may prompt the monitor 40 to retrieve additional control data CD from memory 44 and display it so that the user may page through the various dates and times that have been saved. If no additional histories are available, the user will be notified by monitor 40, for example a "no more history" indicator may be displayed within the history bar (FIG. 6I).

Figure 6F:
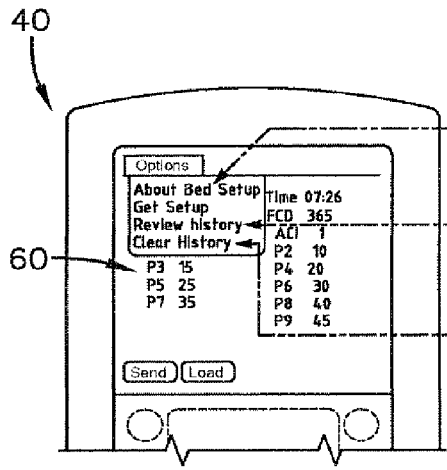
Figure 6G:
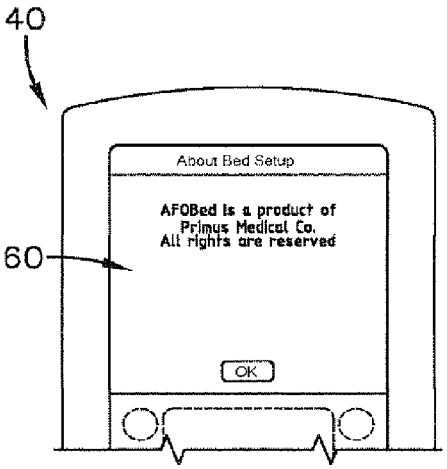
Figure 6H:
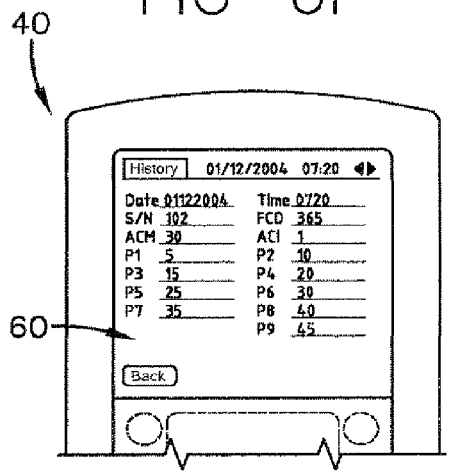
Figure 6I:
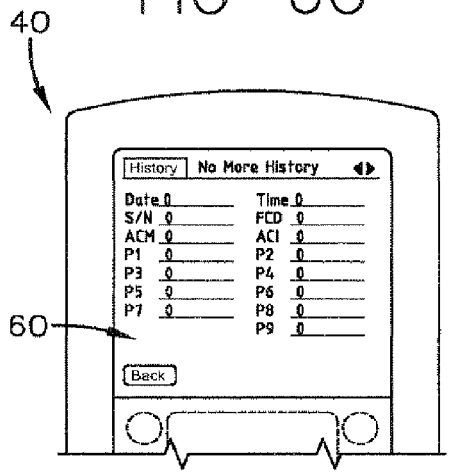
Figure 6J:
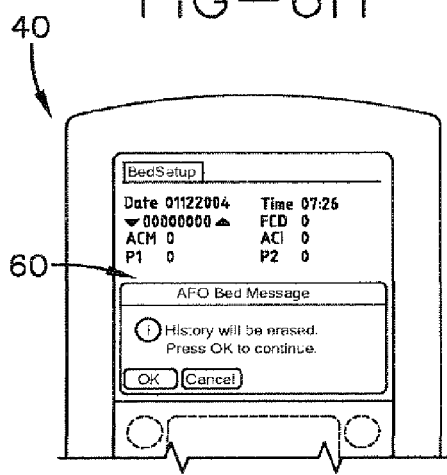
Figure 6K:
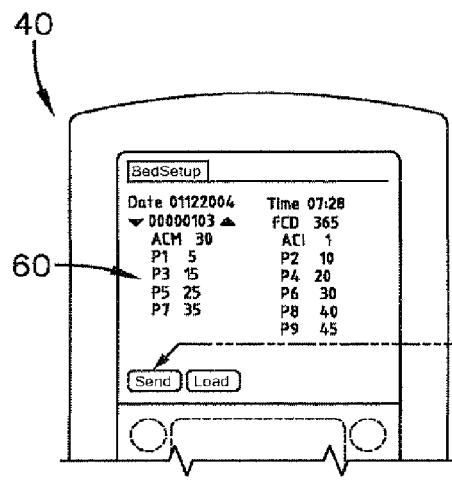
Figure 6L:
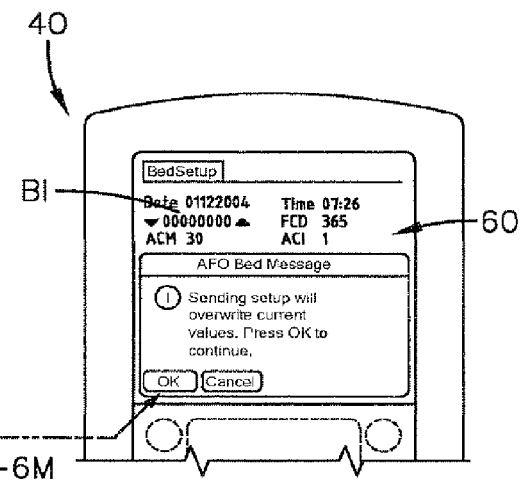
Figure 6M:
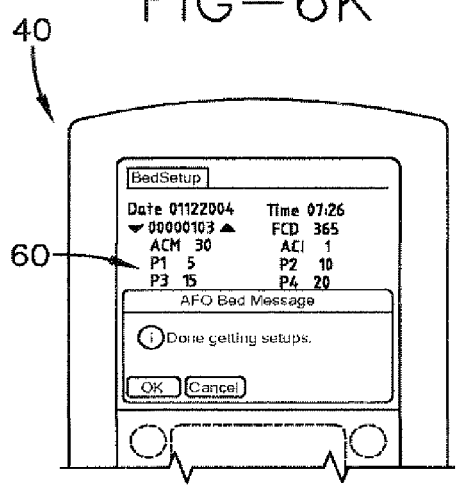

If the user wishes to clear the bed's history, removing it from memory, a "clear history" command may be provided in the pull down menu (FIG. 6F). Again, to avoid inadvertent deletion of histories, the user may be prompted for confirmation before the history is cleared (FIG. 6J).

As depicted in the accompanying Figures, the graphical user interface 60 may be provided on a display screen of portable monitor 40, such as a personal digital assistant, hand held computer, personal entertainment device, such as an IPOD®, or cell phone to provide the user with the greatest convenience. In addition, by using a hand held device, the user may use the same device to change the settings on a number of beds stored in its memory. This eliminates the cumbersome process of individually removing chips and reprogramming their settings. In addition to providing a more convenient process for monitoring and setting multiple beds, the system has greater flexibility in setting up a number of beds. The system permits the caregiver to adjust settings to accommodate different weight capacities without changing blowers. In this way, it is not necessary to stock multiple blowers that are programmed for different weight capacities. Also, when system 10 includes pressure feedback, the controller 25 detects the actual pressure and adjusts the blower speed to account for the difference in the actual pressure and target pressure. In this way, blower decline, which would cause existing systems to be inaccurate i.e. the target pressure would not equal the actual pressure, is overcome by using the controller 25 to adjust the blower speed in response to changes in the actual pressure.

In light of the foregoing, it should thus be evident that a mattress monitoring system according to the concepts of the present invention substantially improves the art. While, in accordance with the patent statutes, only the preferred embodiment of the present invention has been described in detail hereinabove, the present invention is not to be limited thereto or thereby. It will be appreciated that various modifications may be made to the above-described embodiment without departing from the spirit of the invention. Therefore, to appreciate the scope of the invention, reference should be made to the following claims.

What is claimed is:

1. A computer readable medium in a portable monitor for a mattress monitoring system that includes a mattress controller, the portable monitor having computer executable instructions for performing a method comprising:
   (a) maintaining a data structure for a bed identification and one or more control data associated with said bed identification;
   (b) selectively linking with the mattress controller to retrieve a current control data from the mattress controller, and
   (c) comparing the current control data from the mattress controller to the control data maintained in the portable monitor.

2. The computer readable medium in a portable monitor having computer executable instructions for performing the method of claim 1 further comprising:
   updating the control data maintained in the portable monitor based on the current control data from the mattress controller.

3. A portable monitor for monitoring a mattress system that includes a mattress controller, the portable monitor, comprising:
   a memory;
   an input/output node adapted to communicate with the mattress controller;
   a processor programmed to maintain in said memory a data structure including a bed identification and a control data associated with said bed identification, wherein the processor is utilized to:
   selectively link with the mattress controller;
   prompt the controller for a current control data;
   receive computer readable information from the mattress controller to update the control data stored in the data structure; and
   control a display to report the control data to the user.

4. The portable monitor of claim 3, wherein said input/output node includes a wireless transceiver.

5. The portable monitor of claim 3, wherein said input/output node communicates with the mattress controller via a cable connected to said input/output node.

6. The portable monitor of claim 3 further comprising a connector attachable to the mattress controller and the input/output node to establish communication therebetween.

7. The computer readable medium in a portable monitor having computer executable instructions for performing the method of claim 1, the data structure further includes one or more user history logs associated with said bed identification.

8. The computer readable medium in a portable monitor having computer executable instructions for performing the method of claim 1, further comprising altering at least one of the one or more control data based on a mattress pressure feedback.

9. A monitoring system for a mattress, comprising:
a controller that monitors and stores control data related to the mattress;
a portable monitor that receives the control data from the controller, the monitor includes, a transceiver that facilitates wireless communication of the control data between the portable monitor and the controller;
a display to present the control data; and
a selection device that is used to update one or more control data values presented on the display, the one or more updated control data values are transmitted to the controller via the transceiver.

10. The monitoring system of claim 9, wherein control data communication is initiated when the portable monitor is within a predefined distance from the controller.

11. The monitoring system of claim 10, wherein the control data presented on the display is the same as the control data on the controller upon initiation of data communication.

12. The monitoring system of claim 9, further including:
a control input that allows adjustment of control data related to one or more mattress functions.

13. The monitoring system of claim 9, wherein the display allows adjustment of the same control data as the controller interface.

14. The monitoring system of claim 9, wherein the control data is related to one or more operational settings of the mattress.

15. The monitoring system of claim 9, wherein the portable monitor receives one or more notifications when maintenance is required for the mattress.

16. The monitoring system of claim 15, wherein maintenance information includes one or more of a time increment for filter replacement, a maximum alternate cycle, an alternate cycle increment and a pressure setting.

17. The monitoring system of claim 9, wherein the control data is related to one or more of a bed identifier, a serial number, a set time, a set cycle, a time range, a set cycle time interval, and a pressure settings.

18. A method to monitor a mattress, comprising:
logging control data related to the mattress via a controller;
communicating the logged control data wirelessly to a portable monitor;
altering the control data on the portable monitor; and
communicating the altered control data to the controller.

19. The method of claim 18, wherein control data communication is initiated when the portable monitor is within a predefined distance from the controller.

20. The method of claim 18, further including:
altering data logged via the controller using a controller interface; and
altering data on the portable monitor using a display, wherein the controller interface and the display are substantially identical.

\* \* \* \* \*